United States Patent [19]

Miller

[11] Patent Number: 4,986,264
[45] Date of Patent: Jan. 22, 1991

[54] KNEE BRACE

[76] Inventor: Marion E. Miller, 4800 N. A-1-A unit 418, Vero Beach, Fla. 32963

[21] Appl. No.: 414,531

[22] Filed: Sep. 29, 1989

[51] Int. Cl.$^5$ .............................................. A61F 5/00
[52] U.S. Cl. .................................................. 128/80 C
[58] Field of Search ....................... 128/80 C, 80 F, 88

[56] References Cited

U.S. PATENT DOCUMENTS

| | | | |
|---|---|---|---|
| 4,433,679 | 2/1984 | Mauldin et al. | 128/80 F |
| 4,502,472 | 3/1985 | Pansiera | 128/80 F |
| 4,524,764 | 6/1985 | Miller et al. | 128/88 |
| 4,632,096 | 12/1986 | Harris | 128/80 F |
| 4,649,906 | 3/1987 | Spademan | 128/80 C |
| 4,697,583 | 10/1987 | Mason et al. | 128/80 F |
| 4,732,143 | 3/1988 | Kausek et al. | 128/88 |
| 4,791,916 | 12/1988 | Paez | 128/80 C |

Primary Examiner—Richard J. Apley
Assistant Examiner—Glenn Richman
Attorney, Agent, or Firm—Irving M. Kriegsman

[57] ABSTRACT

A knee brace having an anterior tibial shell and an anterior femoral shell which are closely configured to the shape of the lower leg and thigh respectively and which are joined by a frame in the form of a pair of polycentric hinge joints. Each one of the joints includes an upper bar and a lower bar, the two bars being pivotally interconnected. The anterior tibial shell and the anterior femoral shell are both pivotally mounted on the upper bars of the polycentric hinge joints, the anterior femoral shell being mounted above the anterior tibial shell. Because the anterior tibial shell is mounted on the upper bars of the two joints when the knee brace is mounted on the leg of a person and the knee is bent the anterior tibial shell will move downward and inward against the tibia so as to counteract forward directed forces applied to the tibia and thereby provide additional support for the knee. The knee brace also includes a pair of derotation cuffs removably mounted on the femoral and tibial shells for internally rotating the femur and externally rotating the tibia, respectively.

10 Claims, 5 Drawing Sheets

KNEE BRACE

BACKGROUND OF THE INVENTION

The present invention relates generally to orthotics and more particularly to a knee brace which is constructed to provide anterior-posterior, medial-lateral and rotational stability.

Knee braces for providing anterior-posterior, medial-lateral and rotational stability of the knee are well known in the art. Such braces generally include a tibial shell which is constructed so as to be closely configured to the shape of the lower leg and a femoral shell which is constructed so as to be closely configured to the shape of the thigh area of the leg. The two shells are secured to their respective areas on the leg and are interconnected by some type of mechanism so as to pivot relative to each other as the knee is bent. The mechanism is usually a pair of hinge joints, one on each side of the knee brace, with the tibial shell being attached to the lower part of each one of the two hinge joints and the femoral shell being attached to the upper part of each one of the two hinge joints.

For example, in U.S. Pat. No. 4,733,656 to S. Marquette there is disclosed a knee brace having an anterior tibial shell and a posterior femoral shell which are closely configured to the shape of the lower and thigh areas of the leg, the two shells being joined by a closed support band system which is constructed to closely track knee flexion. The band system includes upper vertical uprights and lower vertical uprights which are pivotally interconnected to each other. The femoral shell is attached to the upper vertical uprights while the tibial shell is attached to the lower vertical uprights. The brace also has anteriorly extending tabs positioned between the patella and the femoral epicondyles. The combination of two shells, the band system and the two tabs provides anterior-posterior, medial-lateral and rotary stability.

An another example, in U.S. Pat. No. 4,773,404, to J. H. Townsend there is disclosed an appliance for controlling an unstable knee joint in the sagitall, coronal and transverse planes, comprising femoral and tibial cuffs joined by femoral and tibial links which are interconnected to provide a novel mechanical joint wherein camming slots are formed in one of the links with cams disposed on the other link, the slots comprising straight segments and arcuate segments so as to provide approximately 8 millimeters of sliding movement between the femur and tibia, followed by relative rotation about the center of radius of the femoral condyle as the leg is flexed. The tibial cuff is conformed about the boney prominence or shin or the tibia to inhibit rotation of the leg beneath the knee within the brace itself.

As still another example, in U.S. Pat. No. 4,732,143, to Kauset et al there is disclosed a knee brace which includes a thigh plate, a shin plate and a pair of polycentric hinge joints. Each hinge joint includes an upper arm which is fixed to the thigh plate and a lower arm which is fixed to the shin plate.

It is an object of this invention to provide a new and improved orthopedic appliance.

It is another object of this invention to provide a new and improved knee brace.

It is yet another object of this invention to provide a knee brace that provides anterior-posterior, medial-lateral and rotational stability.

It is still another object of this invention to provide a knee brace that provides increased protection against anterior tibial forces.

It is a further object of this invention to provide a new and improved polycentric hinge joint.

SUMMARY OF THE INVENTION

A knee brace for providing anterior-posterior, medial-lateral and rotational stability of the knee constructed according to the teachings of the present invention comprises a frame, the frame being in the form of a pair of mechanical joints, one of the mechanical joints being disposed at the medial side of the leg and the other mechanical joint being disposed at the lateral side of the leg, each one of the mechanical joints comprising an upper bar and a lower bar, the upper bar being pivotally interconnected to the lower bar in each joint, a relatively rigid anterior tibial shell conforming to the shape of the lower leg, the anterior tibial shell being pivotally mounted on the upper bars of the two mechanical joints, a relatively rigid anterior femoral shell conforming to the shape of the thigh area of the leg, the anterior femoral shell being pivotally mounted on the upper bars of the two mechanical joints above the anterior tibial shell, upper and lower derotation cuffs removably mounted on the femoral and tibial shells respectively for pulling laterally on the calf area and medially on the thigh area, respectively, upper and lower anterior strap assemblies and upper and lower posterior strap assemblies for aiding in securing the leg in the two shells of the knee brace and upper and lower rigid bands fixedly mounted on said upper and lower pairs of bars respectively of the two mechanical joints for fixing the two mechanical joints relative to each other.

Various features and advantages will appear from the description to follow. In the description, reference is made to the accompanying drawing which forms a part thereof, and in which is shown by way of illustration, a specific embodiment for practicing the invention. This embodiment will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

The present invention is directed to a knee brace for protecting the knee against anterior-posterior, medial-lateral and rotational instabilities. The knee brace includes a tibial shell for fitting over the front of the lower leg, a femoral shell for fitting over the front of the thigh area of the leg and a frame for supporting the two shells, the frame comprising a pair of hinge joints each including upper and lower bars and wherein the tibial shell is attached to the frame in a unique manner so as to provide increased protection against a forward directed force applied to the back of the tibia. The present invention achieves this increased protection by attaching the tibial shell to the upper bars of the two hinge joints. As a result of this arrangement for attaching the tibial shell to the frame, when the knee is bent the tibial shell will be pushed downward and inward on the tibia so as to counteract forward directed forces applied to the back of the tibia. According to another feature of the invention, a pair of derotation cuffs are removably mounted on the two shells so a to concurrently externally rotate the tibia and internally rotate the femur.

Figure 1:
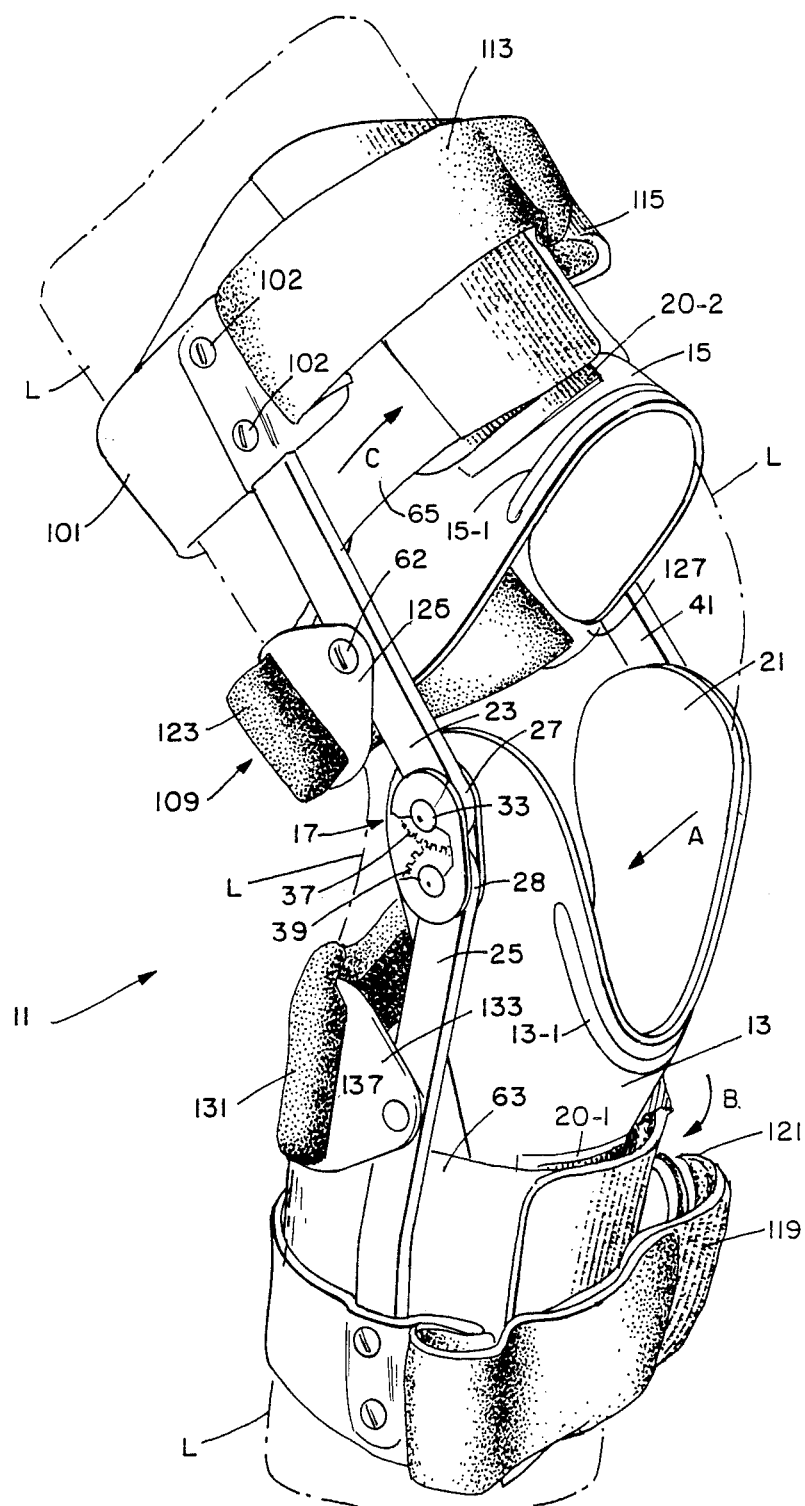
FIG. 1 is a perspective view broken away in parts of a knee brace constructed according to the teachings of the present invention and mounted on the right leg of a wearer, with the leg and knee brace being slightly bent.
Figure 2:
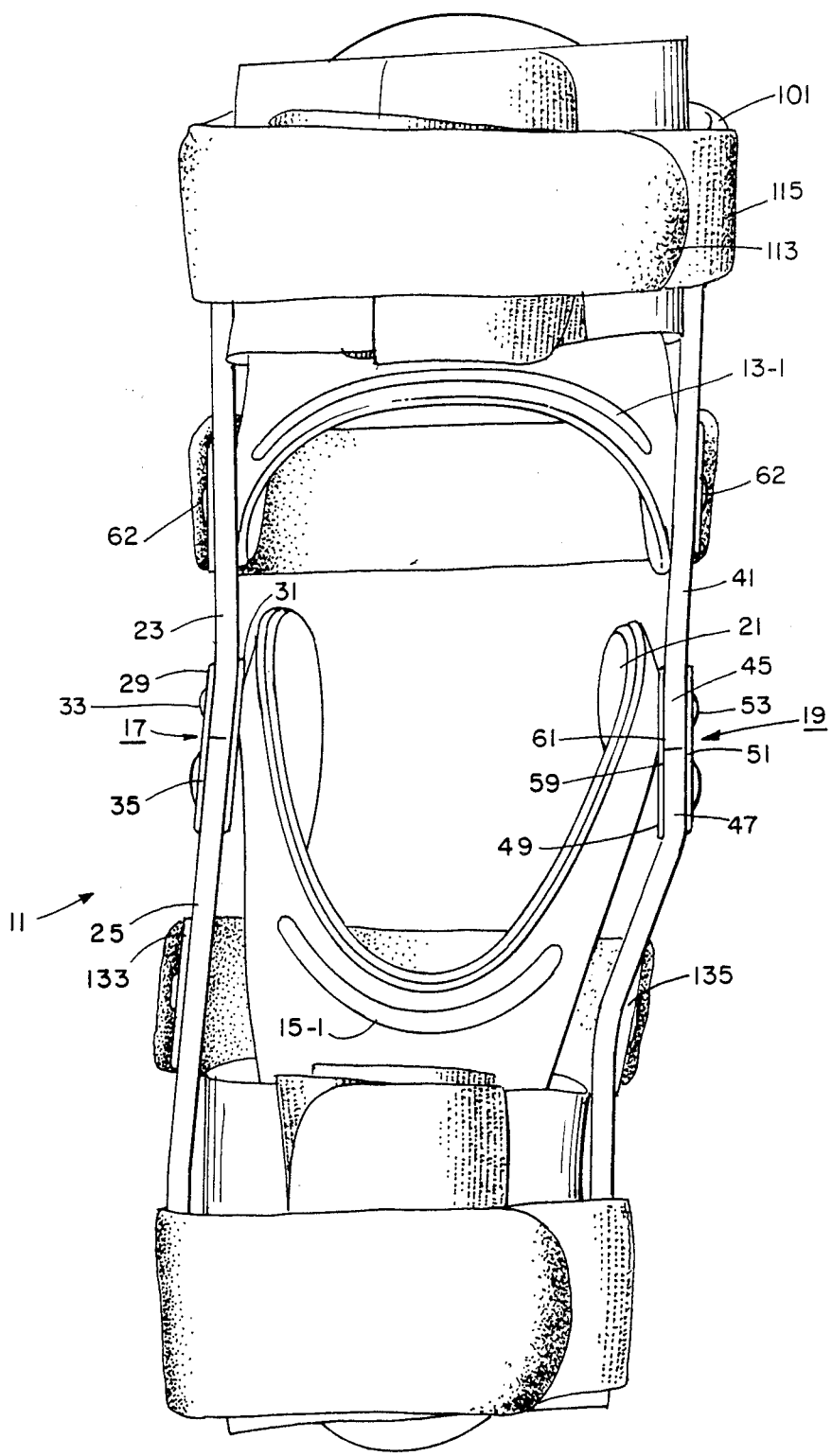
FIG. 2 is a front view of the knee brace shown in FIG, 1, with the knee brace being in a straight (not bent) position.
Figure 2A:
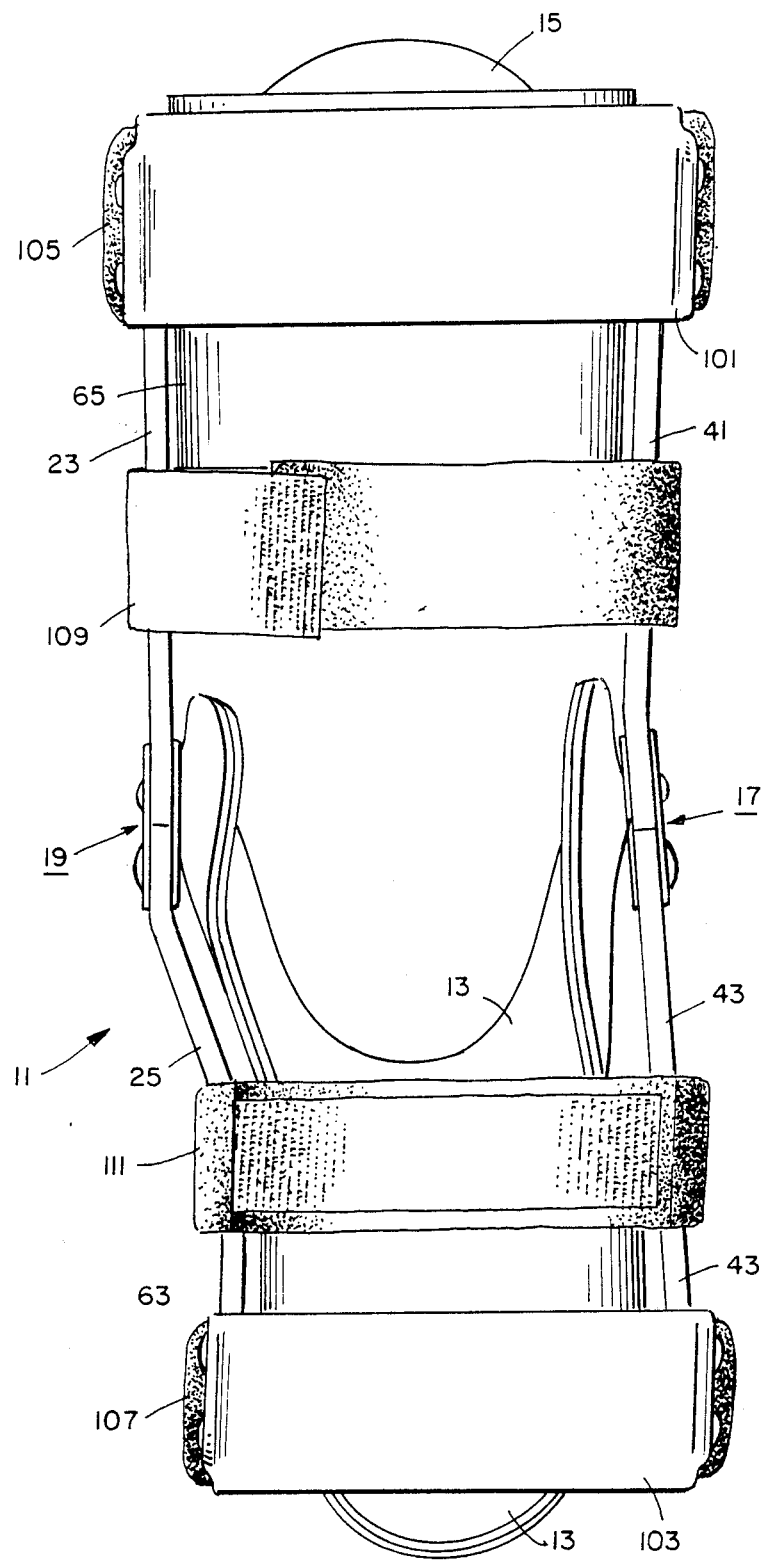
FIG. 2A is a rear view of the knee brace shown in FIG. 2.

Referring now to the drawings, and first to FIGS. 1, 2 and 2A there is shown perspective, front and rear views respectively of a knee brace constructed according to the teachings of the present invention, the knee brace being identified generally by reference numeral 11. For illustrative purposes only, knee brace 11 is a knee brace constructed for use on the right leg of a wearer and in FIG. 1 is shown as so mounted on the right leg L.

Knee brace 11 includes an anterior tibial shell 13 shaped to fit over the front side of the lower leg of the wearer, an anterior femoral shell 15 shaped to fit over the front side of the thigh area of the leg of the wearer and a frame for supporting the two shells 13 and 15 in their appropriate positions, the frame comprising lateral and medial polycentric hinge joints 17 and 19, respectively.

Figure 3:
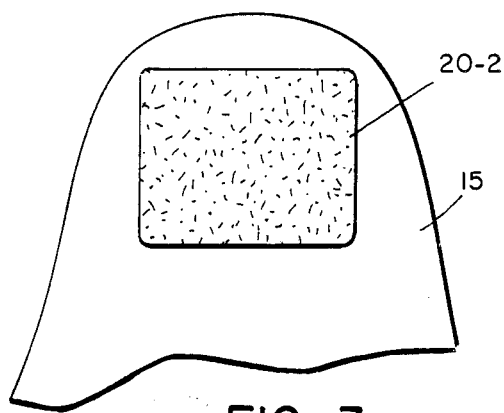
FIG. 3 is a plan view taken from the front of the lower portion of the tibial shell.
Figure 4:
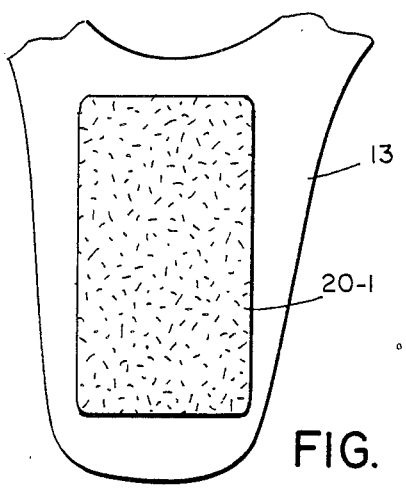
FIG. 4 is a plan view taken from the front of the upper portion of the femoral shell.

Shells 13 and 15, which are also shown in part separately in FIGS. 3 and 4 are made of a relatively rigid material, such as polypropylene and are shaped to include stiffening ribs 13-1 and 15-1, respectively. Shell 13 is preferably lined with a layer 21 of a suitable resilient shock absorbing material such as polyethylene foam. A Velcro pad 20-1 is fixedly mounted such as by glue (not shown) on the front of shell 13 and a Velcro pad 20-2 is fixedly mounted such as by glue (not shown) on the front end of shell 15, the two pads 20 being used for a purpose to be hereinafter explained.

Lateral polycentric hinge joint 17 includes upper and lower bars 23 and 25, respectively, made of a rigid material such as stainless steel. The lower end 27 of bar 23 and the upper end 28 of bar 25 are disposed between a pair of parallel spaced apart face plates 29 and 31, also made of stainless steel. Ends 27 and 28 are pivotally secured to face plates 29 and 31 by rivets 33 and 35 which extend through aligned apertures in face plates 29 and 31 and ends 25 and 27, the two rivets 33 and 35 defining the two pivot axes of the polycentric joint. Rivets 33 and 35 have shouldered heads and pass through brass bushings (not shown) to provide pivotal movements. Ends 27 and 28 of bars 23 and 25 are shaped to define gear teeth 37 and 39 at their edges which mesh with one another so as to cause simultaneous pivotal movement of bars 23 and 25 about their pivotal connections within face plates 29 and 31.

Medial polycentric hinge joint 19 includes upper and lower bars 41 and 43 made of stainless steel. The lower end 45 of bar 41 and the upper end 47 of bar 43 are disposed between a pair of parallel spaced apart face plates 49 and 51 also made of stainless steel. Ends 45 and 47 are pivotally secured to face plates 49 and 51 by rivets 53 and 55 which extend through aligned apertures in face plates 49 and 51 and ends 45 and 47. Rivets 53 and 55 have shouldered heads. Ends 45 and 47 of bars 41 and 43 are shaped to define gear teeth 59 and 61 at their edges which mesh with one another so as to cause simultaneous pivotal movement of bars 41 and 43 about their pivotal connections within face plates 49 and 51. Except for the shape of bar 43, polycentric hinge joint 19 is identical to polycentric hinge joint 17.

Anterior tibial shell 13 is pivotally mounted on bars 23 and 41 at lower ends 27 and 45. Anterior tibial shell 13 is pivotally mounted on bars 23 and 41 by the same rivets 33 and 53 used to mount bars 23 and 41 to face plates 29, 31 and 49, 51. Thus, rivets 33 and 53 also extend through aligned apertures (not shown) in tibial shell 13. Rivets 33 and 53 are appropriately longer than rivets 35 and 55 and are peened over at their far ends (not shown) on the inside of tibial shell 13 while rivets 35 and 55 are peened over at their far ends on the outside of plates 31 and 51.

Anterior femoral shell 15 is pivotally mounted on bars 23 and 41 above anterior tibial shell 13 by rivets 62 which extend through aligned apertures (not shown) in bars 23 and 41 and shell 15.

Because anterior tibial shell 13 is mounted on upper bars 23 and 41 (rather than lower bars 24 and 43) when knee brace 11 is bent anterior tibial shell 13 will move downward and inward against the tibia (in the leg) in the direction shown by arrow A in FIG. 1 counteracting forward direction forces applied to the back of the tibia.

Knee brace 11 further includes a pair of derotation cuffs 63 and 65 which are removably mounted on anterior tibial shell 13 and anterior femural shell 15, respectively. Derotation cuff 63 is removably mounted on anterior tibial shell 13 in a manner so as to pull laterally on the lower leg and thereby externally rotate the tibia in the direction shown by arrow B in FIG. 1 while derotation strap 65 is removably mounted on anterior femoral shell 15 in a manner so as to pull medially on the thigh area of the leg in order to internally rotate the femur in the direction shown by arrow C in FIG. 1.

Figure 5:
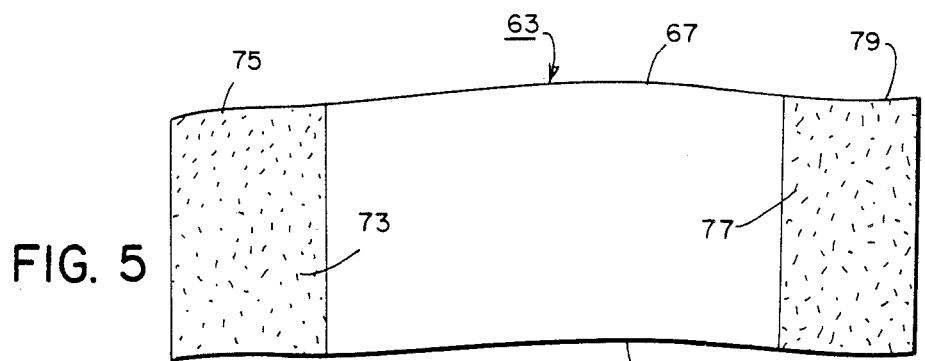
FIG. 5 is a plan view taken from the front of the lower derotation cuff shown in FIG. 2.
Figure 6:
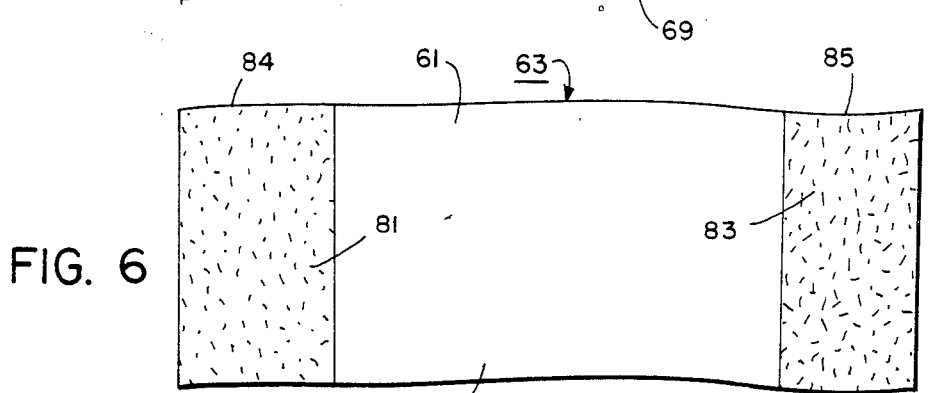
FIG. 6 is a plan view taken from the rear of the lower derotation strap shown in FIG. 2.

Cuffs 63 which is also known separately in FIGS. 5 and 6 includes a strip 67 of an elastic material such as Latex rubber. Strip 67 has a front side 69 and a back side 71. A Velcro pad 73 is fixedly attached to front side 69 at left end 75 and a Velcro pad 77 is fixedly attached to front side 69 at right end 79. A pair of Velcro pads 81 and 83 are also fixedly attached to rear side 71 at left and right ends 84 and 85, respectively.

Derotation cuff 63 is removably mounted on anterior tibial shell 13 and extends back around the leg of the wearer in a clockwise manner. More specifically Velcro pad 73 on strap 63 is first attached to Velcro pad 20-1 on anterior tibial shell 13. After cuff 63 is wrapped around the back of the calf in a clockwise manner and pulled tight, pad 77 is placed over and secured to pad 81.

Figure 7:
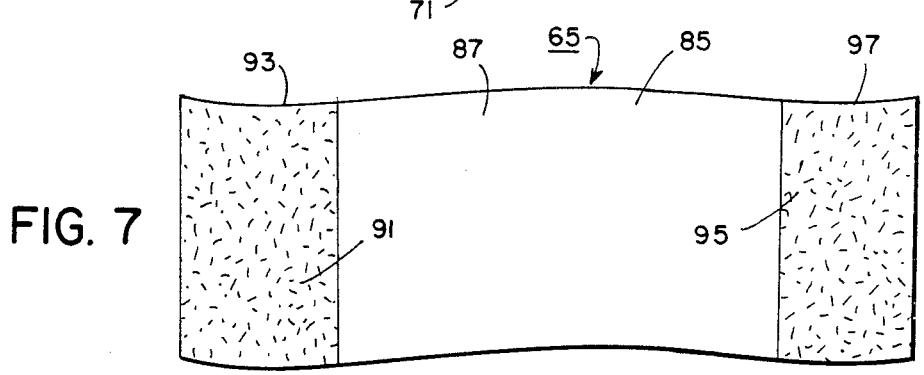
FIG. 7 is a plan view taken from the front of the upper derotation cuff shown in FIG. 2.
Figure 8:
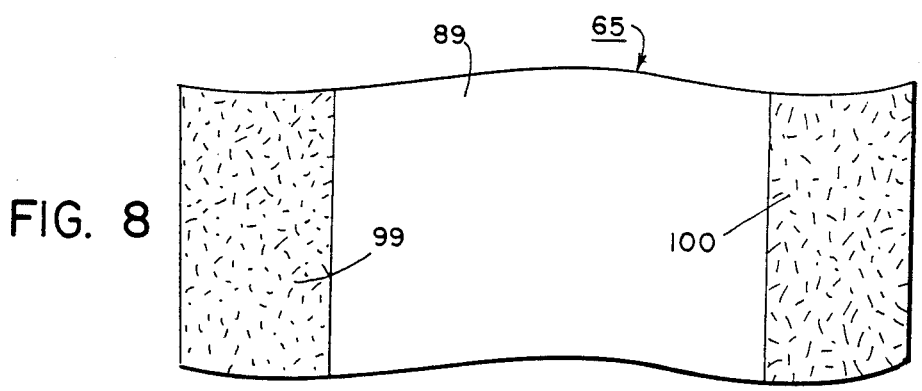
FIG. 8 is a plan view taken from the rear of the upper derotation cuff shown in FIG. 2.

Derotation cuff 65 which is also shown separately in FIGS. 7 and 8 includes a strip 85 of an elastic material such as Latex rubber. Strip 85 has a front side 87 and a back side 89. A Velcro strip 91 is fixedly attached to front side 87 at left end 93 and a Velcro strip 95 is fixedly attached to front side 87 at right end 97. A pair of Velcro pads 99 and 100 also fixedly attached to rear side 89 at left and right ends 93 and 97, respectively.

Derotation cuff 65 is removably mounted on anterior femoral shell 15 and extends back around the thigh of the wearer in a counterclockwise manner. More specifically Velcro pad 95 on strap 65 is first attached to Velcro pad 20-2 on anterior femoral shell 15. After strap 65 is wrapped around the thigh and pulled tight, pad 91 is placed over and secured to pad 101.

An arcuate shaped posterior femoral band 101 made of a rigid material such as polypropylene is fixedly mounted on the upper ends of upper bars 23 and 41 by rivets 102 and serves to maintain upper bars 23 and 41 fixed relative to each other. Similarly, an arcuate shaped posterior tibial band 103 made of a rigid material such as polypropylene is fixedly mounted on the lower ends of lower bars 25 and 43 and serves to maintain lower bars 25 and 43 by rivets 104 fixed relative to each other.

An upper anterior strap assembly 105, a lower anterior strap assembly 107, an upper posterior strap assembly 109 and a lower posterior strap assembly 111 collectively serve to hold knee brace 11 on the leg of the wearer.

Upper anterior strap assembly comprises a pair of straps 105 and 115 having Velcro on each side thereof and which are fixedly secured to the lateral and medial ends, respectively, of posterior femoral band 101, such as by rivets 117. In use strap 115 is placed over and attached to Velcro pad 99 on derotation cuff 63. Strap 113 is then placed over and attached to strap 115.

Lower anterior strap assembly 107 comprises a pair of straps 119 and 12 having Velcro on each side thereof which are fixedly secured to the lateral and medial ends, respectively, of posterior tibial band 103, such as by rivets 117. In use strap 121 is placed over and attached to Velcro strip 95 on derotation strap 65. Strap 119 is then placed over and attached to cuff 121.

Upper posterior strap assembly 109 is adjustable and includes a strap 123 made of flexible material and having Velcro on each side. Strap 123 includes Velcro end strips 123-1 and 123-2 fixed at each end. Strap 123 passes through slots 124 in plastic hangers 125 and 127 which are pivotally mounted on bars 23 and 41 by the same rivets 62 used to attach shell 15 to bars 23 and 41 with the ends of the strap being doubled back on itself and attached to each other at the desired adjustment by the Velcro strips 123-1 and 123-2.

Lower posterior strap assembly 111 is adjustable and includes a strap 131 of flexible material. Strap 131 includes Velcro strips 131-1 and 131-2 fixed at each end. Strap 131 passes through slots 132 in plastic hangers 133 and 135 which pivotally mounted on bars 25 and 43 by rivets 137 with the ends of the strap being doubled back on itself attached to each other at the desired adjustment by the Velcro strips 131-1 and 131-2.

Figure 9:
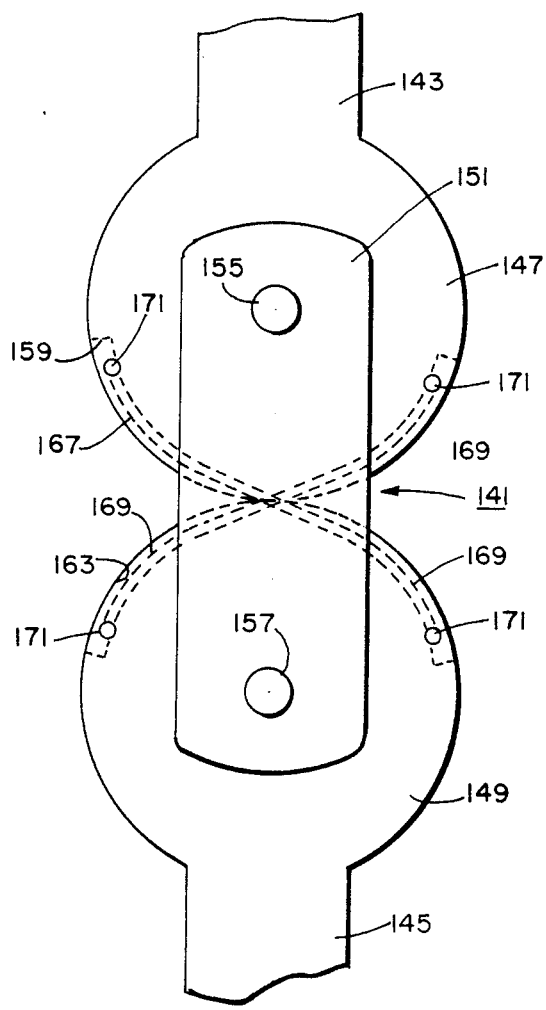
FIG. 9 is an end view of a modification of the hinge joints shown in FIG. 1.
Figure 10:
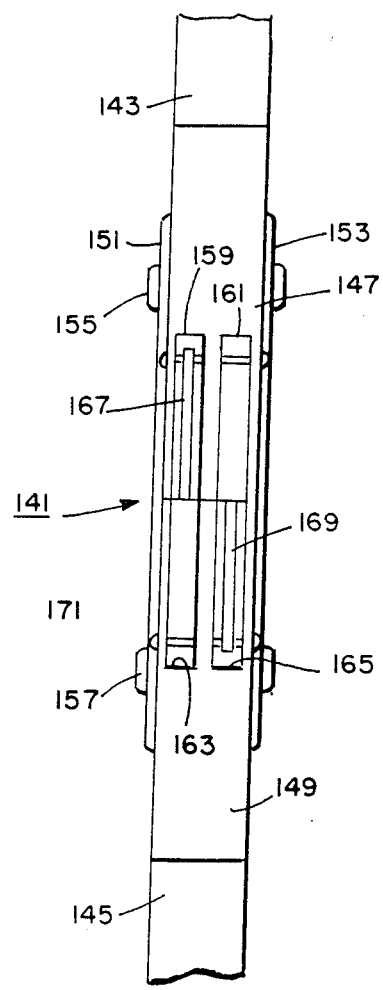
FIG. 10 is a front view of the hinge joint shown in FIG. 0.

Referring now to FIGS. 9 and 10, there is shown end and front views, respectively, of a modification of the polycentric hinge joints shown in FIGS. 1 and 2, wherein the bar members are not shaped to define gear teeth and wherein motion is coordinated by a pair of cables, the modification being identified generally by reference numeral 141.

Polycentric hinge joint 141 includes upper and lower bars 143 and 145, respectively, which are made of a rigid material such as stainless steel. The lower end 147 of bars, which is circularly shaped, and the upper end 149 of bar 145, which is also circularly shaped, are disposed between a pair of parallel spaced apart face plates 151 and 153, which are made of stainless steel. Ends 147 and 149 are pivotally secured to face plates 151 and 153 by rivets 155 and 157. End 147 is shaped to include left and right peripheral channels 159 and 161, respectively, and end 149 is shaped to include left and right peripheral channels 163 and 165, respectively. A cable 167 is disposed in left channels 159 and 163 and extends from the front end of left channel 159 to the rear end of left channel 163. A cable 169 is disposed in right channels 161 and 165 and extends from the rear end of right channel 161 to the front end of right channel 165. Cables 167 and 169 are held in place by rivets 171 and serve to cause simultaneous pivotal movement of the bars and their pivotal connections with the plates. Cables 167 and 169 are made of titanium wire or other suitable material. As can be seen, at any one time only one of the two cables 167 and 169 is in tension, the particular cable depending on which way the joint is bent.

The embodiment of the present invention is intended to be merely exemplary and those skilled in the art shall be able to make numerous variations and modifications to it without departing from the spirit of the present invention. For example, the mechanical joints could be single axis rather than polycentric joints; it only being necessary that tibial shell 13 be pivotally mounted above the anatomical center of the joints. All such variations and modifications are intended to be within the scope of the present invention as defined in the appended claims.

What is claimed is:

1. A knee brace for providing anterior-posterior, medial-lateral and rotational stability of the knee of a person comprising:
   a. a frame, said frame comprising a pair of mechanical joints, one of the mechanical joints being at the medial side of the leg and the other mechanical joint being at the lateral side of the leg, each one of said mechanical joints comprising an upper bar and a lower bar, each upper bar being pivotally interconnected to its associated lower bar,
   b. an anterior tibial shell conforming to the shape of the lower leg pivotally mounted on the upper bars of the two mechanical joints,
   c. an anterior femoral shell conforming to the shape of the thigh area of the leg pivotally mounted on the upper bars of the two mechanical joints above the anterior tibial shell, and
   d. means for securing the thigh and lower leg respectively in the femoral and tibial shells, respectively.

2. The knee brace of claim 1 and further including a pair of derotation cuffs, one of said derotation cuffs being removably mounted on the anterior tibial shell and the other cuff being removably mounted on the femoral shell.

3. The knee brace of claim 1 and further including upper bar connecting means for fixedly connecting the two upper bars relative to each other and lower bar connecting means for fixedly connecting the two lower bars relative to each other.

4. The knee brace of claim 3 and wherein the upper and lower bar connecting means each comprising a band of rigid material.

5. The knee brace of claim 4 and wherein the means for securing the thigh and lower leg in the femoral and tibial shells comprise upper and lower anterior strap assemblies and upper and lower posterior strap assemblies.

6. The knee brace of claim 5 and wherein the two mechanical joints are polycentric hinge joints.

7. The knee brace of claim 6 and wherein the femoral and tibial shells are made of a relatively rigid material.

8. The knee brace of claim 7 and wherein the femoral and tibial shells are made of polypropylene.

9. The knee brace of claim 8 and wherein the upper and lower bar connecting means are made of polypropylene.

10. A polycentric hinged joint for use in orthotic devices comprising:
  a. a pair of parallel spaced apart face plates,
  b. a lower and upper bar each disposed between said pair of parallel spaced apart face plates and pivotally secured to said pair of parallel spaced apart face plates at spaced apart locations, each of said bars having their facing ends arcuately shaped and having means to guide a cable, and
  c. a pair of cables each attached to both of said bars so as to cause simultaneous pivotal movement of the bars about their pivotal connections with the plates.

* * * * *